United States Patent [19]
Grinev et al.

[11] 3,983,141
[45] Sept. 28, 1976

[54] DERIVATIVES OF 5-HYDROXY-6-DILOWERALKYLAMINOMETHYL-BENZOFURANS

[76] Inventors: Alexei Nikolaevich Grinev, ulitsa Volgina, 15, korpus 2, kv. 57, Moscow; Alexandr Alexandrovich Stolyarchuk, ulitsa R. Ljuxemburg, 1, kv. 12, Vinnitsa; Pavel Alexandrovich Galenko-Yaroshevsky, ulitsa Kosmonavtov, 52, kv. 14, Vinnitsa; Vladimir Spiridonovich Tantsjura, ulitsa Litvinenko, 2, kv. 5, Vinnitsa; Natalya Vitalievna Arkhangelskaya, Krasnoprudnaya ulitsa, 26, kv. 36, Moscow, all of U.S.S.R.

[22] Filed: May 13, 1974

[21] Appl. No.: 469,528

[30] Foreign Application Priority Data
  May 18, 1973  U.S.S.R............................. 1924401

[52] U.S. Cl................. 260/346.2 R; 260/247.2 B; 260/268 BC; 260/293.58; 260/326.34; 424/285; 424/248; 424/250; 424/274
[51] Int. Cl.²...................................... C07D 307/84
[58] Field of Search............... 260/346.2 R, 247.2 B

[56] References Cited
OTHER PUBLICATIONS
Grinev et al., Chem. Abstr., vol. 59 (1963), 7466a.
Kumar et al., Chem. Abstr., vol. 62 (1965), 11765e.

*Primary Examiner*—Natalie Trousof
*Assistant Examiner*—Bernard Dentz
*Attorney, Agent, or Firm*—Steinberg & Blake

[57] ABSTRACT

Derivatives of 5-oxy-6-aminomethylbenzofuran having the general formula

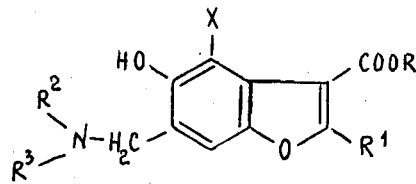

where R is alkyl, R' is alkyl, aryl, R² is alkyl, R³ is alkyl, or R² and R³, together with a nitrogen atom to which they are bonded, form a heterocycle comprising one or two hetero-atoms, and X is a halogen.

Said compounds are prepared by aminomethylation of derivatives of 5-oxybenzofuran having the formula

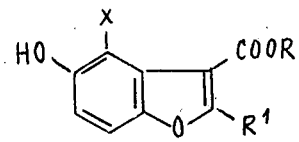

where R is alkyl, R' is alkyl, aryl, and X is a halogen.

The reaction of aminomethylation can be carried out with a substituted bisaminomethane or with a mixture, consisting of a secondary amine and formaldehyde.

Said compounds possess pharmacological activity.

4 Claims, No Drawings

DERIVATIVES OF 5-HYDROXY-6-DILOWERALKYLAMINOMETHYL-BENZOFURANS

This invention relates to derivatives of 5-oxy-6-aminomethylbenzofuran and to the method of preparing the same.

According to the invention, derivatives of 5-oxy-6-aminomethoxyfuran have the following general formula I

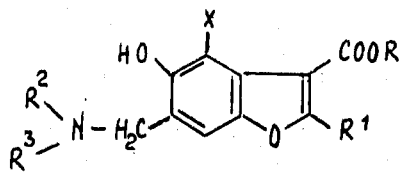

where R is alkyl, R' is alkyl, aryl, R² is alkyl, R³ is alkyl, or R² and R³, together with a nitrogen atom to which they are bonded, form a heterocycle comprising one or two heteroatoms, and X is a halogen.

Said compounds have not been described in the literature.

Derivatives of 5-oxy-6-aminomethylbenzofuran having formula I are stable amphoteric substances, white in colour, and have no odour. They form stable salts with mineral and organic acids, that are soluble in water.

Said compounds are pharmacologically active substances and can therefore be used in medicine. The usefulness of the proposed compounds can be illustrated by one of their representatives, for example, 2-methyl-3-carboethoxy-4-chloro-5-oxy-6-dimethylaminomethyl-benzofuran. This compound, in the form of a salt, can be used as an effective local anesthetic. With respect to its anesthetic action it is superior to novacaine, especially as to the depth and length of its action, when given for infiltration, conduction and cerebrospinal anesthesia.

In experiments on guinea pig (after Buhlbring-Wade) said compound produces a marked infiltration anesthesia. Its aqueous solutions having concentrations of 0.05, 0.1, and 0.25 per cent produce complete loss of sensitivity which lasts 15–20, 40–45 and 120 minutes, respectively. Novocaine, given in a concentration of 0.05 per cent, does not produce any anesthetic action, in the concentration of 0.1 per cent the loss of sensitivity is only partial, and a 0.25 per cent solution of novocaine only produces anesthesia which lasts for 8–14 minutes. When given in the concentration of 0.5 per cent, said compound produces anesthesia which persists for 15–18 hours, and in a concentration of 1 per cent, within 24–30 hours. The same concentrations of novocaine produce anesthetic effect within 15–20 and 40–55 minutes respectively.

In experiments on non-narcotized rabbits, with the use of the 'pain' method, said substance produces partial loss of sensitivity for 14–125 minutes when given in a concentration of 0.05 per cent, for 28–39 minutes in a concentration of 0.1 per cent, and the loss of sensitivity is complete with concentrations of 0.25, 0.5 and 1 per cent for 79–114, 145–156 and 172–235 minutes, respectively. Novocaine, given under the same conditions, produces incomplete loss of sensitivity in concentrations of 0.1, 0.25 and 0.5 and 1 per cent for 7–11, 29–34, 40–53 and 58–69 minutes, respectively.

In experiments on rabbits with conduction anesthesia, the compound produces loss of sensitivity when given in a concentration of 0.25 per cent for 72–90 minutes, in a concentration of 0.5 per cent for 132–155 minutes and in a concentration of 1 per cent for 157–174 minutes. Novocaine in concentrations of 0.5 and 1 per cent, produces loss of sensitivity for 31 – 41 and 48 – 54 minutes, respectively. Moreover, in all these concentrations, said compound produces full loss of sensitivity, while novocaine produces only partial loss of sensitivity.

The comparison of the anesthetic effect of 2-methyl3-carbethoxy-4-chloro-5-oxy-6-dimethylaminomethylbenzofuran and novocaine in cerebrospinal anesthesia has shown that 5 per cent solutions of the proposed substance and of novocaine produce loss of sensitivity in rats. But the proposed substance produces full loss of sensitivity immediately after its administration and persists for 66–76 minutes, while novocaine only decreases the sensitivity and this partial loss of sensitivity lasts for 14 – 16 minutes.

2-Methyl-3-carbethoxy-4-chloro-5-oxy-6-dimethylaminomethylobenzofuran has been used in surgical operations on animals (rabbits and dogs), during which the hind extremeties were removed and the small intestine resected. The anesthesia was prompt and complete. In all cases a 0.25 per cent solution was injected in a single dose of 20 to 80 ml. No side effects were observed during the operation or soon after it. The healing of the operation wound was by first intention and the post-operative period was eventless in all cases.

The substances is low in toxicity. The DMT with single intravenous injection is 90 mg per kg body weight, with intraperitoneal injection 200 mg/kg and with subcutaneous administration 610 mg/kg. The toxicity of novocaine is somewhat higher.

Prolonged administration of the preparation, within ten days, to rats in a dose of 20 mg/kg (subcutaneously) does not produce any appreciable changes in the appearance or behaviour of the animals; nor does it interfere with histological structure of the internal organs of the aminals. No changes in the histological structure of skin or subcutaneous cellular tissue at the site of injection of the preparation were observed. The preparation does not affect the composition of the formed elements of blood, seral proteins, activity of cytochromoxidase and peroxidase in the granular leukocytes. Within the first 90 – 120 minutes following the injection of the preparation, coagulability of blood (thromboelastographic data) increases transiently.

In addition to its local anesthetic action, the preparation of the present invention produces a soft sedative and ganglioblocking action, it increases 20 – 30 per cent the volumentric rate of the coronary blood flow in acute experiments on cats. The preparation removes arrhythmic phenomena caused by strophantine, aconitine, and calcium chloride. When given in small doses of 0.5 – 1 mg/kg the preparation produces a stimulating action on the intestinal peristalsis, and doses to 10 mg/kg relax the muscular tone in the intestine.

Said substance stimulates contractions of an isolated uterus in various experimental animals, but guinea pig uterus is most responsive towards the action of the preparation. In experiments on animals, the sensitivity of the uterus towards the preparation depends on the estrual phase, and also on the species of the animal. As in the experiments on an isolated uterus, the highest sensitivity was revealed in guinea pigs.

According to the invention, the method of preparing derivatives of 5-oxy-6-aminomethylbenzofuran having the formula I, consists in aminomethylation of derivatives of 5-oxybenzofuran having formula II

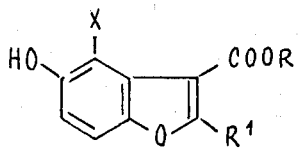

where R is alkyl, R' is alkyl, aryl and X is a halogen.

Aminomethylation of the compounds of formula II is carried out with substituted bisaminomethane or a mixture of a secondary amine with formaldehyde. The starting components for the aminomethylation reaction are taken in stoichiometric ratio.

The reaction between the obtained halogen derivatives of 5-oxy-benzofuran and mineral or organic acids yields salts that are soluble in water.

The synthesis of compounds having the general formula II is carried out by known methods (A. N. Grinev, Pan Bon Khvar, A. P. Terentiev, Zh.O.Kh. 27, 1087, 1957. A. N. Grinev, Pan Bon Khor, A. P. Terentiev, Zh.O.Kh. 27, 821, 1957. C. A. Giza, R. L. Hinman, J. Org. Chem., 29 (6), 1453, 1964.

For a better understanding of the invention, the following examples of its practical embodiment are given by way of illustration.

EXAMPLE 1

Preparation of 2-methyl-3-carbethoxy-4-chloro-5-oxy-6-dimethylaminomethylbenzofuran.

a. A solution of 12.75 g of 2-methyl-3-carbethoxy-4-chloro-5-oxbenzofuran and 8 ml of bis(dimethylamino)methane in 75 ml of anhydrous dioxane is boiled with a reflux condenser for 6 hours and then cooled to 20°C and poured into water. The precipitate is separated on a filter, washed with water and dried. The yield of 2-methyl-3-carbethoxy-4-chloro-5-oxy-6-dimethylaminomethylbenzofuran is 12.6 g (80.5 per cent). M.p. 130°–131°C (from alcohol).

Found, in per cent: C 58.10, H 5.97, N 4.58, Cl 11.26, $C_{15}H_{18}ClNO_4$. Calculated, in per cent: C 57.79, H 5.81, N 4.49, Cl 11.39.

b. A solution of 1.9 g of 2-methyl-3-carbethoxy-4-chloro-5-oxybenzofuran, 2.6 ml of a 33 per cent aqueous solution of dimethylamine and 0.6 ml of a 36 per cent solution of formaldehyde in 12 ml of dimethylformamide is heated with a reflux condenser at a temperature of 100°–105°C for 8 hours, and then cooled to room temperature. The precipitated crystals are separated on a filter, washed with water and dried. The resultant product is 0.75 g of crystalline 2-methyl-3-carbethoxy-4-chloro-5-oxy-6-dimethylaminomethylbenzofuran. The mother liquor is diluted with water to recover an additional 0.4 g portion of crystals. The total yield is 1.15 g (50 per cent); m.p. 130°–131°C (from alcohol). No depression of the melting point is observed in a mixed melting of the obtained crystals with a sample from Example 1 (a).

c. To a solution of 10.1 g of 2-methyl-3-carbethoxy-4-chloro-5-oxy-6-dimethylaminomethylbenzofuran in an anhydrous organic solvent, for example, in ether, added with stirring is a solution of 2.6 g of tartaric acid in 25 ml of alcohol. The precipitate is separated on a filter and re-crystallized from alcohol. The yield of 2-methyl-3-carbethoxy-4-chloro-5-oxy-6-dimethylaminomethylbenzofuran tartrate is 10 g (80 per cent of theory). M.P. 165.5° – 166°C.

Found, in per cent: C 58.02, H 5.41, Cl 9.13, $C_{15}H_{18}ClNO.\frac{1}{2}C_4H_6O_6$. Calculated, in per cent: C 52.78, H 5.48, Cl 9.18.

EXAMPLE 2

Preparation of 2-methyl-3-carbethoxy-4-chloro-5-oxy-6-diethylaminomethylbenzofuran.

The procedure is the same as described in Example 1 (a), except that the reactants are 5.1 g of 2-methyl-3-carbethoxy-4-chloro-5-oxybenzofuran, 4.9 ml of bis(diethylamine)methane, and 25 ml of anhydrous dioxane. The solution is cooled to 20°C and poured into water. The precipitate is separated on a filter, rinsed with water, and dried. The yield of 2-methyl-3-carbethoxy-4-chloro-5-oxy-6-diethylaminomethylbenzofuran is 6.4 g (94 per cent of theory). M.P. 104°–105°C (from alcohol).

Found, in per cent: C 60.20, H 6.47, Cl 10.12, $C_{17}H_{22}ClNO_4$ Calculated, in per cent: C 60.08, H 6.53, Cl 10.44. Hydrochloride, m.p. 168°–170°C (from absolute alcohol). Found, in per cent: Cl 18.74. $C_{17}H_{22}ClNO_4.HCl$. Calculated, in per cent: Cl 18.86.

EXAMPLE 3

Preparation of 2-methyl-3-carbethoxy-4-chloro-5-oxy-6-morpholinomethylbenzofuran.

The reactants are taken in the following quantities: 5.1 g of 2-methyl-3-carbethoxy-4-chloro-5-oxybenzofuran, 5 ml of bismorpholinomethane, and 25 ml of dry dioxane.

The procedure is the same as described in Example 2.

The yield of 2-methyl-3-carbethoxy-4-chloro-5-oxy-6-morpholinomethylbenzofuran is 1.6 g (23 per cent of theory).

Found, in per cent: C 57.68, H 5.75, Cl 10.10. $C_{17}H_{20}ClNO_5$ Calculated, in per cent: C 57.70, H 5.71, Cl 10.03. Hydrochloride, m.p. 219° – 221°C (decomp., from absolute alcohol). Found, in per cent: Cl 18.22, $C_{17}H_{20}ClNO_5.HCl$. Calculated, in per cent: Cl 18.17.

EXAMPLE 4

Preparation of 2-methyl-3-carbethoxy-4-chloro-5-oxy6- [(4'-methylpiperazine)methyl] benzofuran.

The reactants are taken in the following quantities: 5.1 g of 2-methyl-3-carbethoxy-4-chloro-5-oxybenzofuran, 6.8 ml of bis(4-methylpiperazine)methane, and 30 ml of dry dioxane. The reaction product is processed as described in Example 2. The yield of 2-methyl-3-carbethoxy-4-chloro-5-oxy-6(4-methylpiperazine)methylbenzofuran is 4.7 g (65 per cent of theory). M.p 141.5° – 143°C (from methyl alcohol).

Found, in per cent: C 58.95, H 6.30, Cl 9.71, N 7.68. $C_{18}H_{23}ClN_2O_4$. Calculated, in per cent: C 58.93, H 6.32, Cl 9.68, N 7.63. Dihydrochloride, m.p. 259°–261°C (decomp). Found, in per cent Cl 23.88 $C_{18}H_{23}ClN_2O_4.2HCl$. Calculated, in per cent: Cl 24.21.

EXAMPLE 5

Preparation of 2-phenyl-3-carbethoxy-4-chloro-5-oxy-6-dimethylaminomethylbenzofuran.

The reactants are taken in the following quantities: 3 g of 2-phenyl-3-carbethoxy-4-chloro-5-oxybenzofuran, 1.5 ml of bis (dimethylamino)methane and 15 ml of dry dioxane. The procedure is the same as described in Example 2. The yield of 2-phenyl-3-carbethoxy-4-chloro-5-oxy-6-dimethylaminomethylbenzofuran is 3.2 g (90 per cent of theory). M.P 98.5°–100°C (from methyl alcohol).

Found, in per cent: C 64.10, H 5.56, Cl 9.49. $C_{20}H_{20}ClNO_4$ Calculated, in per cent: C 64.24, H 5.4, Cl 9.49. Hydrochloride, m.p. 225°±6°C (decomp., from absolute alcohol). Found, in per cent: Cl 17.14, $C_{20}H_{20}ClNO_4 \cdot HCl$. Calculated in per cent: Cl 17.30.

We claim:

1. A compound of the formula:

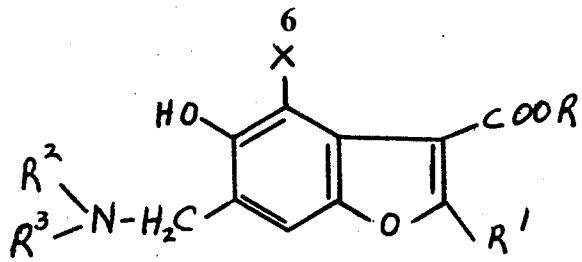

wherein R is lower alkyl, R′ is selected from the group consisting of lower alkyl and phenyl, $R^2$ is lower alkyl, $R^3$ is lower alkyl, and X is halogen, and pharmaceutically acceptable salts thereof.

2. Compound according to claim 1 wherein R′ is lower alkyl.

3. Compound according to claim 1 wherein X is chlorine.

4. 2-methyl-3-carbethoxy-4-chloro-5-hydroxy-6-dimethylaminomethylbenzofuran as claimed in claim 1.

* * * * *